United States Patent [19]

Muto et al.

[11] Patent Number: 4,734,409

[45] Date of Patent: Mar. 29, 1988

[54] CEPHALOSPORIN DERIVATIVE, PROCESS FOR PRODUCING THE SAME AND PHARMACEUTICAL COMPOSITION CONTAINING THE SAME

[75] Inventors: Shigeaki Muto, Tokyo; Chikao Yoshikumi, Kunitachi; Takao Furusho, Machida; Isamu Motokawa, Hino; Yoko Onishi, Mitaka; Akihiko Kanno, Tokyo; Takayoshi Fujii, Tokyo; Takao Ando, Tokyo, all of Japan

[73] Assignee: Kureha Kagaku Kogyo Kabushiki Kaisha, Tokyo, Japan

[21] Appl. No.: 702,135

[22] Filed: Feb. 15, 1985

[30] Foreign Application Priority Data

Feb. 24, 1984 [JP] Japan ................... 59-33972

[51] Int. Cl.$^4$ .................. A61K 31/545; C07D 501/36
[52] U.S. Cl. ..................... 514/206; 540/227
[58] Field of Search .............. 544/27; 514/204, 206; 540/227

[56] References Cited

U.S. PATENT DOCUMENTS

| 4,202,893 | 5/1980 | Heymes et al. | 540/227 |
| 4,258,041 | 3/1981 | O'Callaghan et al. | 544/25 |
| 4,260,607 | 4/1981 | Kakeya et al. | 544/26 |
| 4,278,671 | 7/1981 | Ochiai et al. | 514/203 |
| 4,461,767 | 7/1984 | Brewer et al. | 544/27 |
| 4,510,138 | 4/1985 | Ochiai et al. | 514/206 |
| 4,520,194 | 5/1985 | Ochiai et al. | 540/222 |

FOREIGN PATENT DOCUMENTS 2345153 10/1977 France.
2384781 10/1978 France.
2421904 11/1979 France.

Primary Examiner—Mark L. Berch
Assistant Examiner—William A. Teoli, Jr.
Attorney, Agent, or Firm—Oblon, Fisher, Spivak, McClelland & Maier

[57] ABSTRACT

Disclosed herein are a cephalosporin derivative represented by the formula (I):

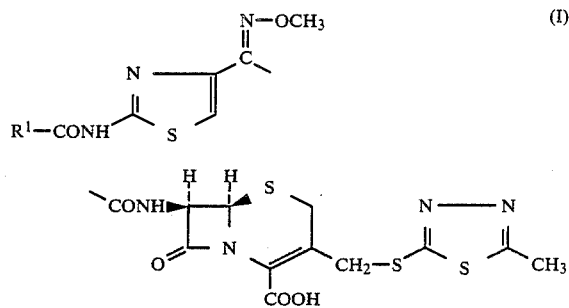

wherein $R^1$ represents a halogenoalkyl group, a salt and ester thereof, a process for producing the same, and a pharmaceutical composition and an antibacterial agent comprising the same.

6 Claims, 2 Drawing Figures

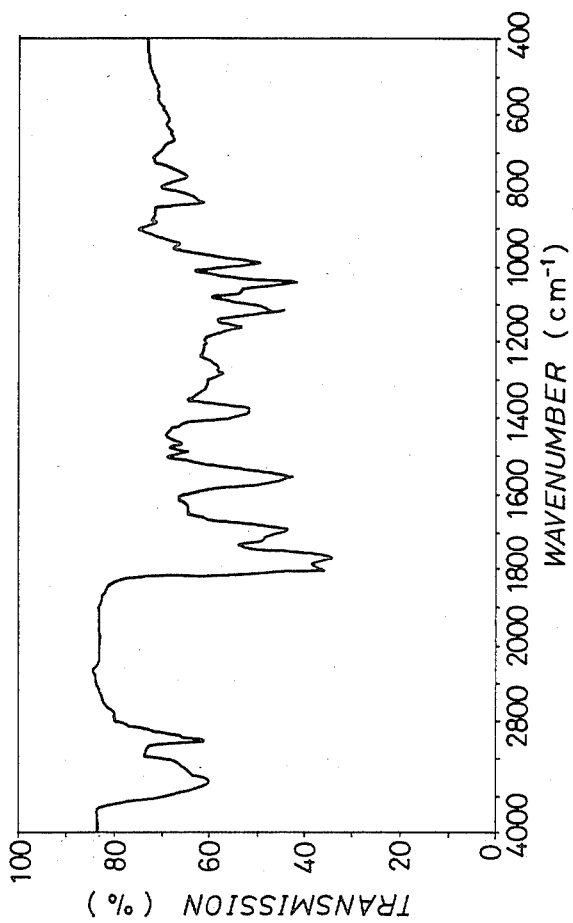

CEPHALOSPORIN DERIVATIVE, PROCESS FOR PRODUCING THE SAME AND PHARMACEUTICAL COMPOSITION CONTAINING THE SAME

BACKGROUND OF THE INVENTION

The present invention relates to a cephalosporin derivative represented by the formula (I):

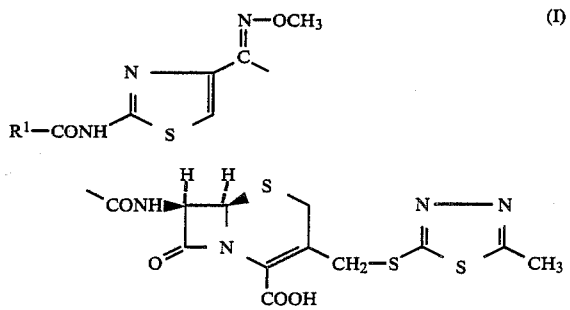

wherein $R^1$ represents a halogenoalkyl group of 1 to 4 carbon atoms, a salt thereof and an ester thereof, and a process for producing the cephalosporin derivative.

The invention also relates to a pharmaceutical composition and antibacterial agent comprising as an active ingredient, the cephalosporin derivative, and a method for the treatment of infectious diseases comprising administering to a patient suffering therefrom a pharmaceutically effective amount of the cephalosporin derivative.

The cephalosporin antibiotics are now broadly used and they are excellent medicines because of their prominent selective toxicity against bacteria. Although the conventional cephalosporins show a broad antibacterial activity against Gram-positive and Gram-negative bacteria while showing a high stability against β-lactamase, they have a serious defect, that is, they show a low stability in blood resulting in a short duration of their antibacterial activity in the living body.

As a result of the present inventors' studies for finding a cephalosporin derivative without showing such a defect, it has been found by the present inventors that a cephalosporin derivative represented by the formula (I) shows a high antibacterial activity and a high stability in blood.

Further, the present inventors have found that an ester of the cephalosporin derivative shows a low antibacterial activity, but the compounds are converted into a free acid thereof, that is, a cephalosporin derivative represented by the formula (I), thereby showing a high antibiotic activity, and have attained the present invention.

Accordingly, the object of the present invention is to provide a cephalosporin derivative showing a prolonged antibacterial activity due to a high stability thereof in blood.

Also, the object of the present invention is to provide the cephalosporin derivative showing a low antibacterial activity in the intestinal tract, however, showing a high and prolonged antibacterial activity due to the conversion into a free acid when absorbed from the intestinal tract into the blood.

SUMMARY OF THE INVENTION

In the first aspect of the present invention, there is provided a novel cephalosporin derivative represented by the formula (I):

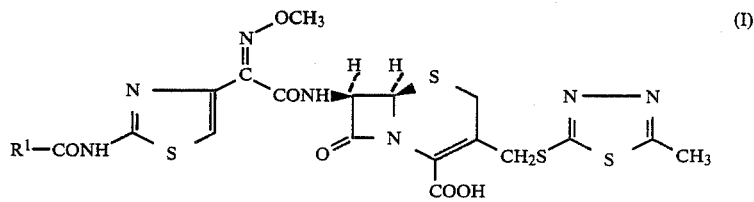

wherein $R^1$ represents a halogenoalkyl group having 1 to 4 carbon atoms, a salt thereof and ester thereof.

In the second aspect of the present invention, there is provided a process for producing a cephalosporin derivative represented by the formula (I):

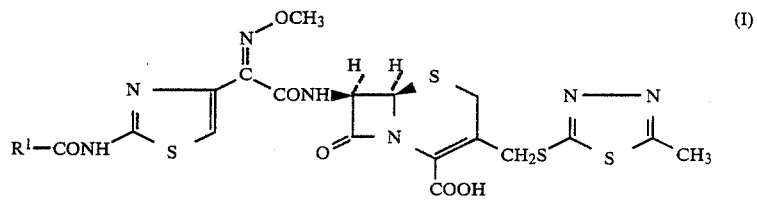

wherein $R^1$ is the same as defined above, and a salt thereof, comprising reacting a compound represented by the formula (II):

wherein $R^1$ is the same as defined above and $R^2$ is a halogen atom or a hydroxy group, with a compound represented by the formula (III):

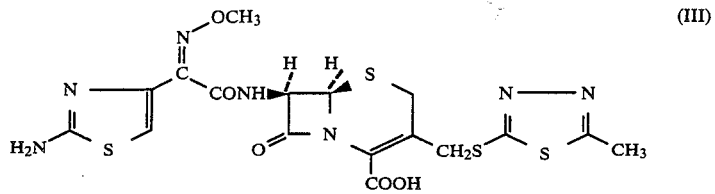
(III)

in an organic solvent at a temperature of −30° to 50° C. for 0.5 to 10 hours.

In the third aspect of the present invention, there is provided a process for producing a cephalosporin derivative represented by the formula (IV):

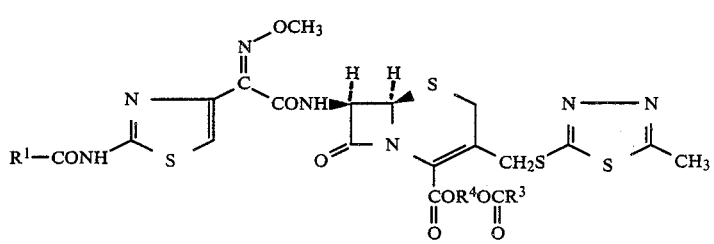
(IV)

wherein $R^1$ represents a halogenoalkyl group having 1 to 4 carbon atoms, $R^3$ represents an alkyl group and $R^4$ represents an alkylene group, comprising reacting a compound represented by the formula (II):

(II)

wherein $R^1$ is the same as defined above and $R^2$ is a halogen atom or a hydroxy group, with a compound represented by the formula (III):

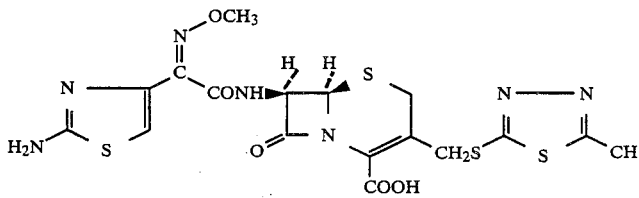
(III)

in an organic solvent at a temperature of −30° to 50° C. for 0.5 to 10 hours, and reacting the thus obtained cephalosporin derivative represented by the formula (I) or a salt thereof with a compound represented by the formula (V):

(V)

wherein X represents a halogen atom and $R^3$ and $R^4$ are the same as defined above, in an organic solvent at a temperature of −30° to 50° C. for 0.5 to 48 hours.

In the fourth aspect of the present invention, there is provided a pharmaceutical composition in a dosage unit form, comprising an effective dosage of a cephalosporin derivative represented by the formula (I),

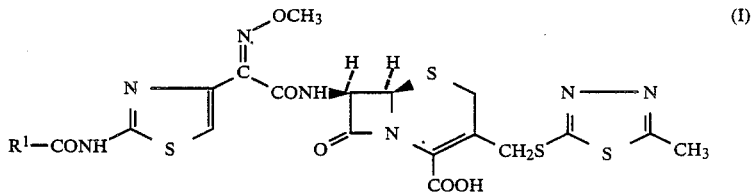
(I)

wherein $R^1$ is the same as defined above, a salt and ester thereof, and pharmaceutically acceptable carrier.

In the fifth aspect of the present invention, there is provided an antibacterial agent comprising, as an active ingredient a cephalosporin derivative represented by the formula (I):

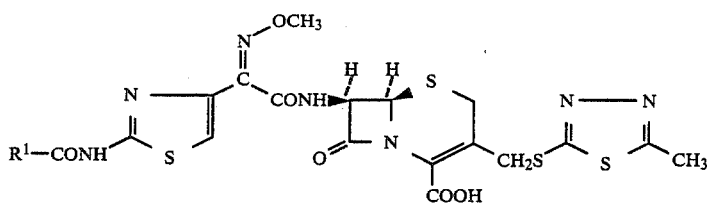

wherein $R^1$ is the same as defined above, a pharmaceutically acceptable salt thereof or an ester thereof.

In the sixth aspect of the present invention, there is provided a method for the treatment of infectious diseases caused by bacteria, which comprises administering to a patient suffering therefrom a pharmaceutically effective amount of a cephalosporin derivative represented by the following formula (I):

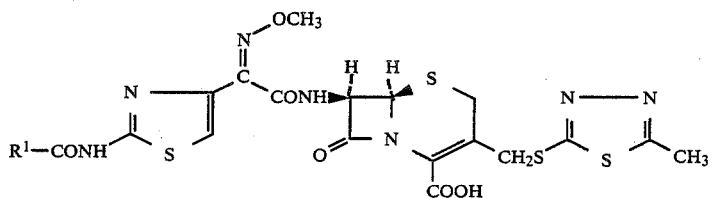

wherein $R^1$ is the same as defined above, a pharmaceutically acceptable salt thereof or ester thereof.

BRIEF EXPLANATION OF DRAWINGS

Of the attached drawings, FIGS. 1 and 2 respectively show the infrared absorption spectra of the cephalosporin derivatives respectively produced in Examples 1 and 2.

DETAILED DESCRIPTION OF THE INVENTION

Figure 1:
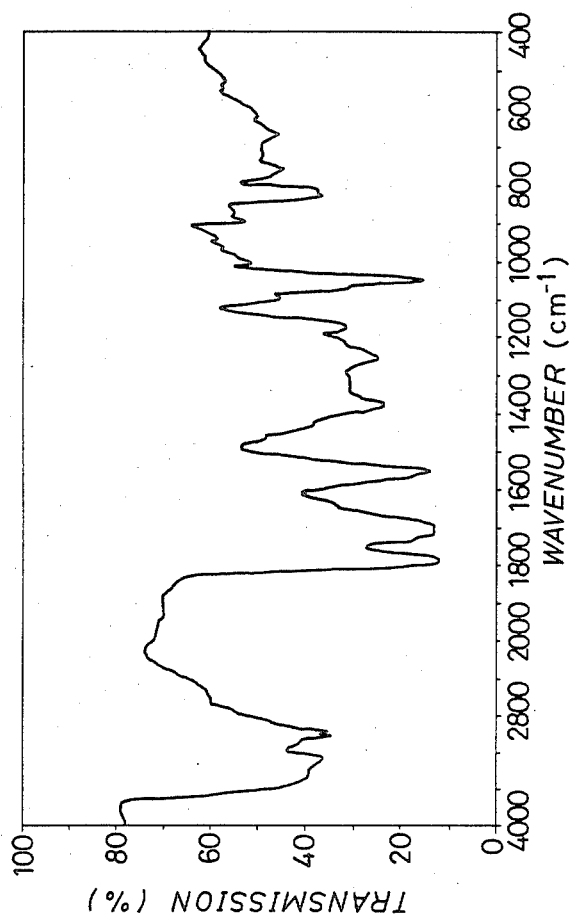

A compound of the present invention (hereinafter referred to as the present compound) is a caphalosporin derivative represented by the formula (I):

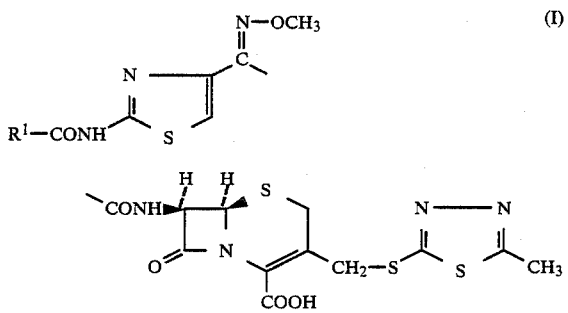

wherein $R^1$ represents a halogenoalkyl group having 1 to 4 carbon atoms, a salt thereof or an ester thereof.

The present compound represented by the formula (I) is prepared by subjecting a compound represented by the formula (III) to a chemical modification and the thus obtained compound shows a prolonged antibacterial activity due to a high stability in blood. Further, the ester prepared from the compound represented by the formula (I) are absorbed from the intestinal tract into the blood without affecting the bacterial colonies in living body and then the ester prepared from the compound represented by the formula (I) show a high antibacterial activity in blood. The salt and ester prepared from the compound represented by the formula (I) are new type antibiotics different from the conventional cephalosporin antibiotics.

The present compound is obtained by the following methods.

(1) A compound, 7β-[2-(2-amino-4-thiazolyl)-(Z)-2-methoxyiminoacetamido]-3-[(2-methyl-1,3,4-thiadiazol-5-yl)thiomethyl]-3-cephem-4-carboxylic acid, represented by the formula (III):

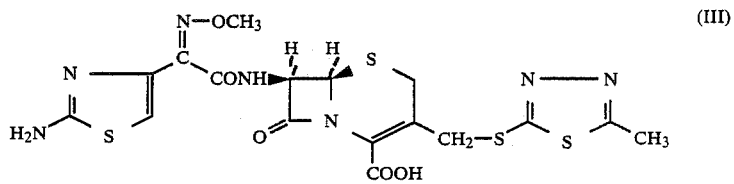

is dissolved in an organic solvent such as acetone, acetonitrile, tetrahydrofuran and dioxane. In this case, it is preferable to add an amine such as triethylamine, dicyclohexylamine and pyridine as an activator into the solution. Into the thus prepared solution, a compound represented by the formula (II):

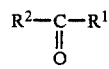

wherein $R^1$ represents a halogenoalkyl group of 1 to 4 carbon atoms and $R^2$ represents a halogen atom or a hydroxy group, is added and the mixture is reacted at a temperature of from −30° to 50° C. for from 0.5 to 10 hours. After the reaction is over, the reaction product is separated and purified by the solvent-extraction, column-chromatography and recrystallization, thereby obtaining the objective product represented by the formula (I). (2) The thus obtained compound represented by the formula (I) or a salt thereof is dissolved in an organic solvent such as dimethylformamide, dimethylsulfoxide, dimethylacetamide and pyridine. In this case, the addition of an amine such as triethylamine and dicyclohexylamine or a base such as sodium hydroxide and sodium hydrogen carbonate into the solution is preferable.

Into the thus prepared solution, a compound represented by the formula (V):

wherein

X represents a halogen atom, $R^3$ represents an alkyl group, for instance, methyl group, ethyl group, propyl group, isopropyl group, butyl group, isobutyl group, s-butyl group, t-butyl group, pentyl group and hexyl group, and $R^4$ represents an alkylene group having 1 to 4 carbon atoms, is added, and the thus prepared mixture was reacted for from 0.5 to 48 hours at a temperature of from $-30°$ to $50°$ C. After the reaction is over, the reaction mixture was separated and purified by washing with a solvent, solvent-extraction, column chromatography and recrystallization to obtain the thus esterified product which is also one of the present compounds represented by the following formula (IV).

for reabsorption, adsorbing carriers, lubricants which are referred herein to as additives exemplified by starch, mannitol, silicic acid, derivatives of cellulose, gelatin, salts of alginic acid, glycerol, agar, calcium carbonate, sodium hydrogen carbonate, paraffin, quarternary ammonium compounds, glycerol monostearate, kaolin, bentonite, talc, potassium stearate, magnesium stearate, polyethylene glycol and the like.

The pharmaceutical composition according to the present invention may take a form of pharmaceutically acceptable emulsion, solution and suspension.

The present compound may be used as an active ingredient in a liquid pharmaceutical composition suitable for oral administration such as a syrup and an elixir containing an inert diluent such as water and/or paraffin. Such a syrup or elixir may contain additives such as wetting agent, sweetener and flavor.

In the case of using the present compound as an active ingredient of sappository, the pharmaceutical composition may contain polyethylene glycol, fatty acid and/or esters thereof.

The pharmaceutical composition comprising the present substance for use in injection may be a sterilized aqueous or non-aqueous solution, emulsion or suspension, and may contain, for instance, propylene glycol, polyethylene glycol, olive oil and the like.

The pharmaceutical composition according to the present invention may contain 0.01 to 99.5% by weight and ordinarily, 0.1 to 90% by weight of the present compound as an active ingredient.

The present compound is used in the same purpose

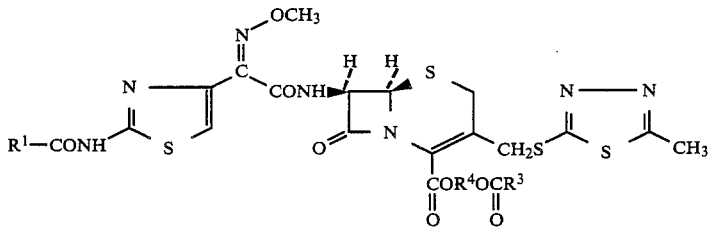

As seen from Examples described below, the present compound has low toxicity and a present compound represented by the formula (I) exhibits an antibacterial activity and shows a high stability in blood. Further, an ester of the compound represented by the formula (I) shows a low antibacterial activity but shows an antibacterial activity when absorbed into living body.

The present compound, a cephalosporin derivative, represented by the formula (I), a salt and ester thereof can be used as an active ingredient of an antibacterial agent or a pharmaceutical composition comprising the present compound and the pharmaceutically acceptable additives such as carrier(s), diluent(s) and adjuvants, and such a pharmaceutical composition may be provided in dosage unit form. Such an antibacterial agent or a pharmaceutical composition can be administered orally, rectally and by injection. For oral administration, the pharmaceutical composition may take a form of powder, granule, tablet, pill, ampoule, etc., which contains fillers, extenders, binders, wetting agents, disintegrating agents, dissolution retarders, accelerators for which a conventional cephalosporin is used, and is effective in treating the infectious diseases caused by bacteria. The dosage of the present compound depends on the extent of infection and the state of the patient, however, a dosage of 0.1 to 10 g, preferably 0.5 to 5 g, may be administered for an adult patient per day, divided into several portions.

The present invention will be more precisely explained while referring to Examples as follows. However, the present invention is not restricted to Examples under mentioned. From the foregoing description, one skilled in the art easily ascertain the essential characteristics of this invention, and without departing from the spirit and scope thereof, can make various changes and modification of the invention to adapt it to various usages and conditions.

EXAMPLE 1

Synthesis of the present compound represented by the following formula:

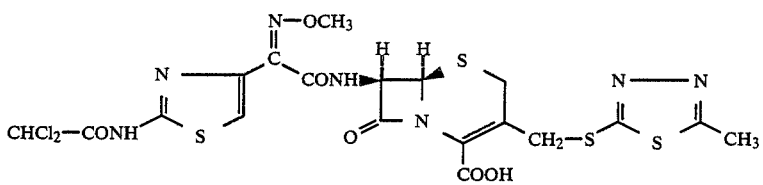

In 100 ml of dry acetone, 2.6 g of 7β-[2-(2-amino-4-thiazolyl)-(Z)-2-methoxyiminoacetamido]-3-[(2-methyl-1,3,4-thiadiazol-5-yl)thiomethyl]-3-cephem-4-carboxylic acid and 1.0 ml of dicyclohexylamine were dissolved, and the solution was cooled to −10° C. After adding dropwise a solution of 0.82 g of dichloroacetyl chloride in 10 ml of acetone to the thus prepared cooled solution, the mixture was stirred for one hour at −10° C. and then stirred for one hour at room temperature. After removing non-soluble matter from the mixture by filtration, the filtrate was evaporated, and 50 ml of ethyl acetate and 25 ml of water were added to the evaporation residue. After washing the organic layer two times with aqueous 2% hydrogen chloride solution and then two times with saturated aqueous solution of sodium chloride, the organic layer was dried over anhydrous magnesium sulfate to remove water. After removing the solvent from the dried solution, the residue was purified by column chromatography on alumina passing aqueous 3% sodium acetate solution as an eluant through the column to obtain 2.4 g of the objective product as crystals in a yield of 75%.

The analytical data of the present compound thus obtained were as follows.

(1) Melting point: 157° to 160° C.

(2) Infrared absorption spectrum (KBr method): shown in FIG. 1, $\nu_{max}(cm^{-1}$: 3250, 3020, 1792, 1705, 1555, 1042.

(3) Ultraviolet absorption spectrum (in methanol): $\lambda_{max}(nm)$: 239, 266.

(4) Elementary analytical data:

|  | C (%) | H (%) | N (%) |
|---|---|---|---|
| Found | 35.70 | 2.58 | 15.40 |
| Calcd. as $C_{19}H_{17}O_6N_7S_4Cl_2$ | 35.74 | 2.66 | 15.36 |

EXAMPLE 2

Synthesis of the present compound represented by the following formula:

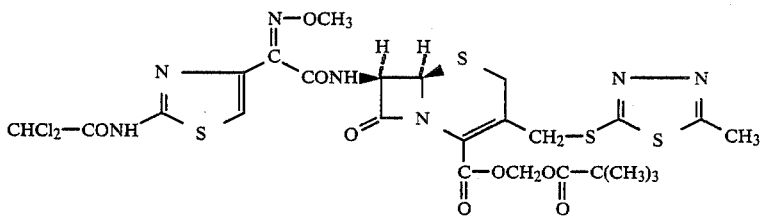

In 26 ml of N,N-dimethylformamide, 2.3 g of 7β-[2-(2-dichloroacetamido-4-thiazolyl)-(Z)-2-methoxyiminoacetamido]-3-[(2-methyl-1,3,4-thiadiazol-5-yl)thiomethyl]-3-cephem-4-carboxylic acid and 0.67 ml of dicyclohexylamine were dissolved, and after adding 1.1 g of bromomethyl t-butyrate to the thus prepared solution, the mixture was stirred for 4 hours at room temperature. After removing insoluble material from the mixture by filtration, the filtrate was decanted two times with each 200 ml of a 2:1 mixed solvent of n-hexane and ether, and after distilling the solvent off, 25 ml of water and 50 ml of ethyl acetate were added to the residue. After washing the organic layer 2 times with aqueous 5% solution of sodium hydrogen carbonate and then 2 times with aqueous saturated solution of sodium chloride, the organic layer was dried over anhydrous sodium sulfate to remove water. After distilling the solvent off from the thus dried organic layer, the residue was purified by column chromatography on silica gel passing a mixed solvent of ethyl acetate and chloroform as an eluant through the column to obtain 0.7 g of the objective product as crystals in a yield of 27.5%.

The analytical data of the present compound thus obtained were shown as follows:

(1) Melting point: 114° to 116° C.

(2) Infrared absorption spectrum (KBr method): shown in FIG. 2, $\lambda_{max}(cm^{-1})$ 3450, 3010, 1796, 1765, 1555, 1118, 1045.

(3) Ultraviolet absorption spectrum (in methanol): $\nu_{max}(nm)$: 240, 268, 262.

(4) Elementary analytical data:

|  | C (%) | H (%) | N (%) |
|---|---|---|---|
| Found | 39.80 | 3.58 | 13.12 |
| Calcd. as $C_{25}H_{27}O_8N_7S_4Cl_2$ | 39.89 | 3.59 | 13.03 |

EXAMPLE 3

Acute toxicity:

Acute toxicity of the present compounds were determined as follows.

Each of the aqueous dispersions of each of the present compounds in an aqueous physiological saline solution at a predetermined concentration was administered to ICR-JCL mice orally by a stomach tube or intraperitoneally by injection. After observing the symptoms of intoxication on each mouse for 7 days after administration, the level of $LD_{50}$ was determined from the mortality during the 7 days while using a graphical method of Litchfield-Wilcoxon. All the mice both survived and died were autopsied to obtain toxicological information. Every one of the present compounds showed the $LD_{50}$ level of larger than 10 g/kg regardless of the route of administration.

EXAMPLE 4

Effect on the intestinal bacterial colonies:

Effect of the present compound on the intestinal bacterial colonies was examined as follows.

The present compound prepared in Example 2 was orally administered to each of 5 animals of a group of female ICR-JCL mice of 6-weeks-old at a daily dosage of 100 mg/kg once a day for continuous 2 days. Feces of each of the mice were collected before and after one day of the administration, and after diluting thereof with 100 times by weight of an anaerobic diluent (an aqueous phosphoric acid buffer) the thus diluted feces were ground, and 0.1 ml of the thus ground and diluted feces was smeared on each culture medium for each bacterial species (shown in Table 1).

After incubating the thus prepared culture media at 25° C. for one to five days aerobically in the cases of *Escherichia coli, Pseudomonas aeruginosa* and the Streptococcus species or anaerobically in the cases of the *Lactobacillus acidophilus, Lactobacillus bifidus* and the Bacterioides species, the number of each bacteria proliferating on the culture medium was counted.

The results of counting the number of each bacteria were shown in Table 2.

TABLE 1

Culture Medium and Culture Conditions of Bacteria Incubated

| Bacterium | Culture medium | Culture Conditions |
|---|---|---|
| (1) *Escherichia coli* | DHL agar | aerobic, 37° C., one day |
| (2) *Pseudomonas aeruginosa* | NAC agar | the same as above |
| (3) *Streptococcus* sp. | TATAC agar | the same as above |
| (4) *Lactobacillus acidophilus* | LBS agar | anaerobic, 37° C., 5 days |
| (5) *Lactobacillus bifidus* | BS agar | the same as above |
| (6) *Bacteroides* sp. | NBGT agar | the same as above |

TABLE 2

| | Logarithmic value of the number of bacterial cells per one gram of feces | | | | | |
|---|---|---|---|---|---|---|
| | (1) *E. coli* | (2) *P. aeruginosa* | (3) *Streptococcus* sp. | (4) *L. acidophilus* | (5) *L. bifidus* | (6) *Bacteroides* sp. |
| before administration | 6.4 | <3.0 | 6.8 | 9.0 | 8.5 | 8.3 |
| after administration | 6.4 | <3.0 | 7.0 | 8.9 | 8.5 | 8.2 |

As is seen in Table 2, the number of each bacteria after administration of the present compound was nearly the same as that before administration thereof, namely, the present compound does not exhibit any influence on the intestinal bacterial colonies

EXAMPLE 5

Antibacterial activity:

Antibacterial activity of the present compound was examined by agar plate dilution method while following the standard method of Japan Society of Chemotherapy and using the following strain:

1. *Escherichia coli* IFO 12734
2. *Staphylococcus aureus* IAM 1011
3. *Escherichia coli* W 3636
4. *Proteus vulgaris* IAM 1025
5. *Pseudomonas aeruginosa* IAM 1514
6. *Serratia marcescens* IAM 1223

Namely, after inoculating each bacteria on Mueller-Hinton culture medium, the inoculum was incubated for 18 to 48 hours at 37° C. and after adjusting the number of cells of each bacteria so as to contain $10^6$ in one ml, the thus prepared specimen was used as the test bacterial liquid.

Each of the present substances (the substance in Example 1 and the substance in Example 2) was dispersed in aqueous physiological saline solution at a predetermined concentration and the thus prepared dispersion was added to 9 times by volume of the culture medium for examining sensitivity (Mueller-Hinton culture medium) to prepare agar plates.

On each agar plate, each of the test bacterial liquid was smeared at a width of about 2 cm, and the thus smeared agar plate was incubated for 18 to 24 hours at 37° C. The concentration of the present substance at which the growth of the bacterial species was completely inhibited was called the minimal inhibitory concentration (MIC), the results being shown in Table 3.

TABLE 3

| Present Compound | *E. coli* IFO 12734 | *S. aureus* IAM 1011 | *E. coli* W 3636 | *Pro. vulgaris* IAM 1025 | *P. aeruginosa* IAM 1514 | *S. marcescens* IAM 1223 |
|---|---|---|---|---|---|---|
| Example 1 | 0.1 | 0.78 | 0.4 | 0.05 | 50 | 0.4 |
| Example 2 | 50 | ≧100 | ≧100 | 50 | ≧100 | ≧100 |

As seen from Table 3, the present compound prepared in Example 1 shows an antibacterial activity and the compound may, therefore, be useful as an antibiotic. On the other hand, the present compound prepared in Example 2, an ester of the compound of Example 1, shows a low antibacterial activity and further the ester compound of Example 2 shows a possibility to be used as an oral antibiotic agent.

EXAMPLE 6

Activation in the living body:

The following experiment was carried out in order to prove that the present compound had a high antibacterial activity in a living body.

As an enzyme for activating metabolism of the present compound, rat liver homogenate (S-9, manufactured by Oriental Yeast Co., Ltd.) was used in preparing the following mixture (hereinafter referred to as S-9 mix).

| Composition of S-9 mix (amount in one ml of S-9 mix) | |
|---|---|
| 0.5 ml | S-9 |
| 3.3 μmol | Potassium chloride |
| 8 μmol | Magnesium chloride hexahydrate |
| 5 μmol | Glucose-6-phosphate |
| 4 μmol | NADH |
| 4 μmol | NADPA |
| 0.5 ml | 0.2 M phosphoric acid buffer (pH 7.4) |

A test solution of present compound was prepared by mixing 0.1 ml of a dispersion of the present compound and 0.9 ml of the thus prepared S-9 mix and shaking the thus prepared mixture for 20 min at 37° C. As a control, a mixture was prepared by mixing 0.1 ml of the dispersion of the present compound and 0.9 ml of the 0.2M phosphoric acid buffer and shaking the mixture for 20 min at 37° C.

As the test bacteria, Staphylcoccus aureus IAM 1011 was inoculated in Mueller-Hinton culture medium and after incubating the inoculum for 18 hours at 37° C., the number of the bacteria was adjusted to $10^8$/ml and the bacterial preparation was mixed with 50 times by volume of Mueller-Hinton culture medium, and an agar plate was prepared from the mixture.

After placing a penicillin cup of 8 mm in diameter on the thus prepared agar plate, 0.1 ml of the test solution of present compound prepared above was put into the cup, and after leaving the agar plate for 2 hours at 4° C., the agar plate was subjected to culture for 18 hours at 37° C. and the diameter of a proliferation-inhibiting circle appearing on the agar plate was measured.

The same procedures were carried out except for using 7β-[2-(2-amino-4-thiazolyl)-(Z)-2-methoxyiminoacetamido]-3-[(2-methyl-1,3,4-thiadiazol-5-yl)thiomethyl]-3-cephem-4-carboxylic acid used as a starting compound in Example 1 instead of the present compound.

The percentage of the diameter of a proliferation-inhibiting circle due to the present compound to that due to the starting compound mentioned above was obtained, and from the following standards, the degree of activation was obtained. The results are shown in Table 4.

TABLE 4

| Present compound tested | Degree of activation | |
|---|---|---|
| | Before adding S-9 mix | After adding S-9 mix |
| Product of Example 1 | ++++ | ++++ |
| Product of Example 2 | ± | ++++ |
| Standard | | |
| − | | 0% |
| ± | | 0 to 1% |
| + | | 1 to 33% |
| ++ | | 33 to 66% |
| +++ | | 66 to 100% |
| ++++ | | 100 to 150% |

EXAMPLE 7

Stability of the present compound in the living body:

As a model experiment for verifying the stability of the present compound in Example 1 in the living body, the following procedures were adopted.

The same test solution of the present compound as in Example 6 was prepared by mixing 0.1 ml of the dispersion of the present compound and 0.9 ml of S-9 mix, and shaking the mixture for 20 min at 37° C. As a control, a mixture of 0.1 ml of the dispersion of the present compound and 0.9 ml of the 0.2M phosphoric acid buffer was shaken for 20 min at 37° C.

As the test bacteria, Staphylococcus aureus IAM 1011 was inoculated in Mueller-Hinton culture medium, and after incubating the inoculum for 18 hours at 37° C., the number of bacteria in the medium was adjusted to $10^8$/ml and the thus adjusted, cultured medium was mixed with 50 times by volume of Mueller-Hinton culture medium. After preparing an agar plate from the mixture, a penicillin cup of 8 mm in diameter was placed on the agar plate, and 0.1 ml of the test solution prepared above was put into the cup. After leaving the thus prepared agar plate for 2 hours at 4° C., the agar plate was subjected to culture for 18 hours at 37° C. to measure the diameter of a proliferation-inhibiting circle appearing on the agar plate. From a calibration curve preliminarily prepared between the concentration of the present compound and the diameter of the proliferation-inhibiting circle, the concentration of the present compound in the test solution and the control was obtained. By using the thus obtained concentration, the rate of retaining the antibacterial activity (Rate (%)) was calculated from the following formula and is shown in Table 5.

$$\text{Rate (\%)} = 100 \times \frac{\text{Concentration of the present compound in the mixture after mixing with S-9 mix}}{\text{Concentration of the present compound in the mixture as the control}}$$

As a comparative experiment, the same precedures were carried out except for using Cefotax (a commercialized cephalosporin derivative sold by CHUGAI Pharmaceuticla Co., Ltd., which is represented by the following formula),

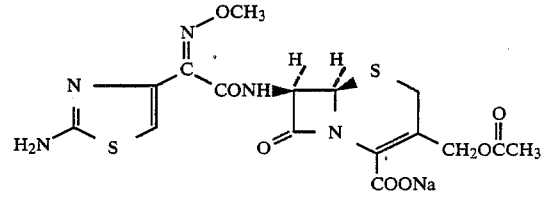

Cefotax instead of the present compound produced in Example 1. Rate was calculated in a similar manner as above and is also shown in Table 5.

TABLE 5

| Compound | Rate of retaining the antibacterial activity (%) |
|---|---|
| Present compound produced in Example 1 | 90 |
| Cefotax | 17 |

As is seen in Table 5, the present compound produced in Example 1 is superior to a conventional commercialized cephalosporin derivative in the rate of retaining the antibacterial activity in the living body.

In the same experiment as above except for using the present compound produced in Example 2, the same result as that obtained in using the present compound produced in Example 1 was obtained in the case where the substance was mixed with S-9 mix.

EXAMPLE 8

Therapeutic effect on the experimental infectious disease on mice:

Therapeutic effect of the present compounds on the infection was examined as follows.

After inoculating $1.4 \times 10^3$ cells of *Escherichia coli* IFO 12734 intraperitoneally to each of a group consisting of 20 ddY-SPF mice to infect the animal, the present compound produced in Example 2 was orally administered 1 time, just 1 hour after the inoculation at a dosage of 25 mg/kg, and the mortality of the animals due to the infection was observed for 7 days.

Although all the mice (inoculated and not administered) died on the second day after inoculation, all the mice administered with the present compound survived even after 7 days after inoculation.

All the ddY-SPF mice administered with the present compound produced in Example 1 via intravenation survived after 7 days after inoculation.

As seen from the result of the above experiment, the present compound produced in Example 2 shows a prolonged antibacterial activity in the living body.

EXAMPLE 9

Preparation of a pharmaceutical composition:

A tablet was prepared by a following composition in one tablet of 200 mg;

| | |
|---|---|
| the present compound of Example 2 | 175 mg |
| lactose | 16 mg |
| starch | 5 mg |
| hydroxypropylcellulose | 3 mg |
| magnesium stearate | 1 mg |

The present compound and lactose was mixed and then an aqueous solution of hydroxypropylcellulose was admixed, and the mixture was kneaded, dried and pulverized. Then magnesium stearate dispersed previously into starch was admixed and the mixture was made into a tablet by the conventional method for tabletting.

What is claimed is:

1. A cephalosporin compound represented by the formula IV:

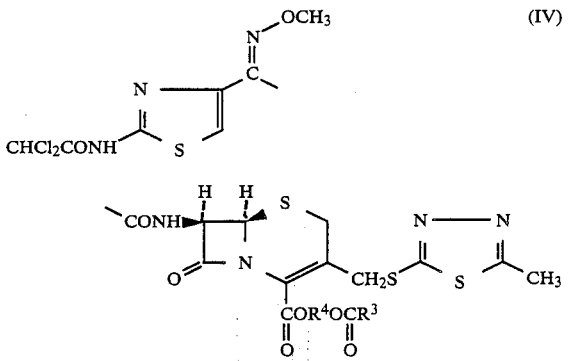

wherein $R^3$ represents an alkyl group having 1 to 6 carbon atoms and $R^4$ represents an alkylene group having 1 to 4 carbon atoms.

2. A cephalosporin compound according to claim 1, which is a compound represented by the following formula:

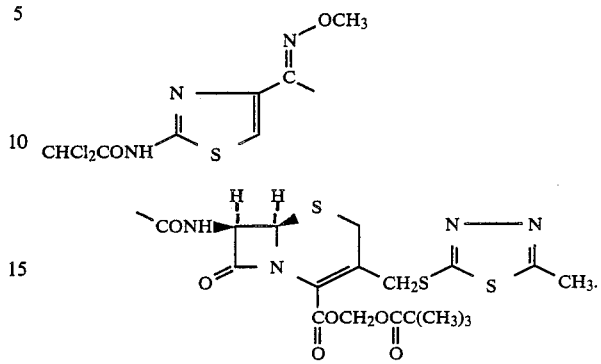

3. An antibacterial composition in a dosage unit form, comprising a pharmaceutically effective amount of a cephalosporin compound represented by the formula (IV):

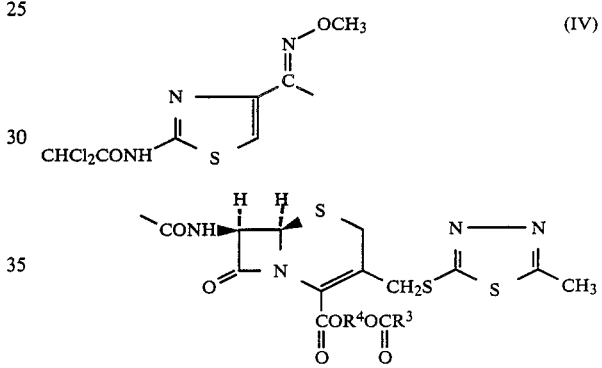

wherein $R^3$ represents an alkyl group having 1 to 6 carbon atoms and $R^4$ represents an alkylene group having 1 to 4 carbon atoms, and pharmaceutically acceptable carrier.

4. An antibacterial composition according to claim 3, wherein said cephalosporin compound is a compound represented by the following formula:

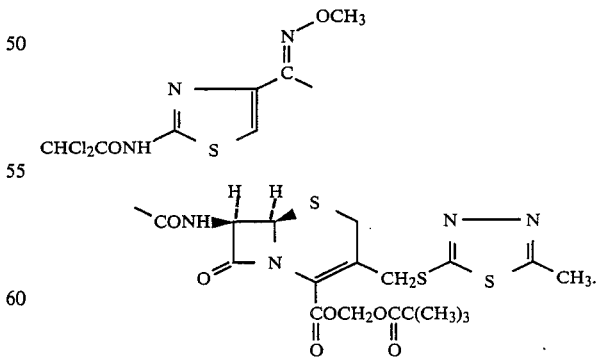

5. A method for the treatment of infectious diseases caused by bacteria, which comprises administering to a patient suffering therefrom a pharmaceutically effective amount of a cephalosporin compound represented by the following formula (IV):

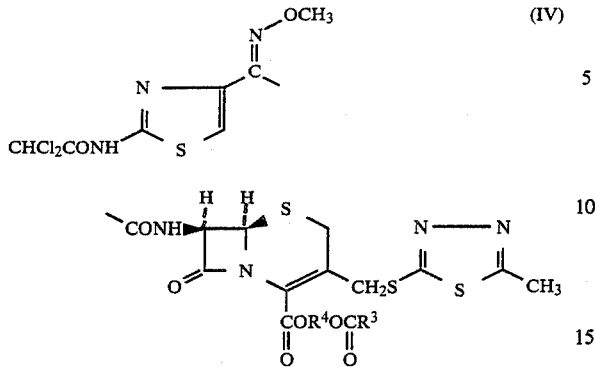
(IV)
wherein R³ represents an alkyl group having 1 to 6 carbon atoms and R⁴ represents an alkylene group having 1 to 4 carbon atoms.
6. A method according to claim 5, wherein said cephalosporin compound is a compound represented by the following formula:
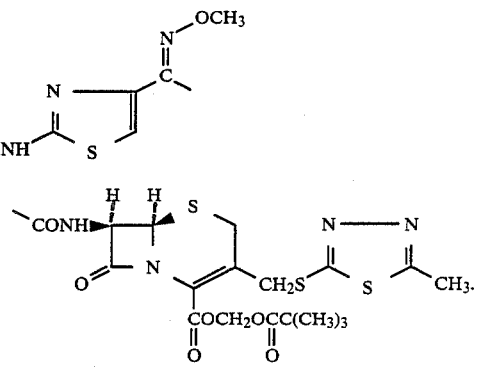
* * * * *